US00PP08985P

United States Patent [19]

VandenBerg

[11] Patent Number: Plant 8,985

[45] Date of Patent: Nov. 22, 1994

[54] CHRYSANTHEMUM PLANT NAMED VALERIE

[75] Inventor: Cornelis P. VandenBerg, Salinas, Calif.

[73] Assignee: Yoder Brothers, Inc., Barberton, Ohio

[21] Appl. No.: 155,236

[22] Filed: Nov. 22, 1993

[51] Int. Cl.[5] ..... A01H 5/00

[52] U.S. Cl. ..... Plt./76

[58] Field of Search ..... Plt. 76, 81

[56] References Cited

U.S. PATENT DOCUMENTS

Plt. 8,607 2/1994 VandenBerg ..... Plt. 76

*Primary Examiner*—Howard J. Locker

*Attorney, Agent, or Firm*—Foley & Lardner

[57] ABSTRACT

A Chrysanthemum plant named Valerie particularly characterized by its flat capitulum form; decorative capitulum type; dark red-purple ray floret color; diameter across face of capitulum of 34 to 44 mm when fully opened; branching pattern is spreading, with 6 to 8 breaks after pinch when grown outside under natural daylength in fall flowerings and 5 to 6 breaks when grown in 10 cm pots for spring flowerings; natural season flower date of September 2 to 7 when planting rooted cuttings on June 18 to 10 in Salinas, Calif., and of October 7 to 14 when planting rooted cuttings June 15 to June 18 in Hightstown, N.J.; flowering response of 54 to 58 days after rooting in no light/no shade programs in spring in Salinas; plant height of 28 to 30 cm when grown in fall under natural daylength with no growth regulators in New Jersey, and of 15 to 18 cm when grown in 10 cm pots in spring with no growth regulator applications; and recommended as late-season variety for October sales.

3 Drawing Sheets

The present invention comprises a new and distinct cultivar of Chrysanthemum, botanically known as *Dendranthema grandiflora,* and referred to by the cultivar name Valerie.

Valerie, identified as 8792 (90-857001), was originated from a cross made by Cornelis P. VandenBerg in a controlled breeding program in Salinas, Calif., in April 1990.

The female parent of Valerie was the cultivar identified as Bravo, a red decorative garden mum disclosed in U.S. Plant Pat. No. 6,888.

The male parent of Valerie was the cultivar identified as Emily, a light pink decorative garden mum with darker center of the flower and many disc florets, disclosed in U.S. Plant Pat. No. 7,754.

Valerie was discovered and selected as one flowering plant within the progeny of the stated cross by Cornelis P. VandenBerg in January 1991, in a controlled environment in Salinas, Calif.

The first act of asexual reproduction of Valerie was accomplished when vegetative cuttings were taken from the initial selection in April 1991 in a controlled environment in Salinas, Calif., by technicians working under supervision of Cornelis P. VandenBerg.

Horticultural examination of controlled flowerings of successive plantings has shown that the unique combination of characteristics are herein disclosed for Valerie are firmly fixed and are retained through successive generations of asexual reproduction.

Valerie has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Valerie, which, in combination, distinguish this Chrysanthemum as a new and distinct cultivar:

1. Flat capitulum form.
2. Decorative capitulum type.
3. Dark red-purple ray floret color.
4. Diameter across face of capitulum of 35 to 44 mm when fully opened.
5. Branching pattern is spreading, with 6 to 8 breaks after pinch when grown outside under natural daylength in fall flowerings, and 5 to 6 breaks when grown in 10 cm pots for spring flowerings.
6. Natural season flower date of September 2 to 7 when planting rooted cuttings on June 18 to 19 in Salinas, Calif., and October 7 to 14 when planting rooted cuttings June 15 to June 18 in Hightstown, N.J.
7. Flowering response of 54 to 58 days after rooting in no light/no shade programs in spring in Salinas.
8. Plant height of 28 to 30 cm when grown in fall under natural daylength with no growth regulators in New Jersey, and 15 to 18 cm when grown in 10 cm pots in spring with no growth regulator applications.
9. Recommended as late-season variety for October sales.

The accompanying photographic drawings show typical inflorescence and leaf characteristics of Valerie, with the colors being as nearly true as possible with illustrations of this type.

Sheet 1 is a color photograph of Valerie grown outside in Salinas, Calif. and dug and transplanted into 15 cm bulb pans at flowering time for photography purposes.

Sheet 2 is a black and white photograph of three views of the inflorescence of Valerie.

Sheet 3 is a black and white photograph showing the upper and under sides of the leaves of Valerie at 3 stages of development (mature, intermediate and immature). In sheets 2 and 3 a measuring tape in centimeters has been added.

Of the commercial cultivars known to the inventor, the most similar in comparison to Valerie is the cultivar identified as Barbara, disclosed in U.S. Plant Pat. No. 8,607. Reference is made to attached Chart A, which compares certain characteristics of Valerie to the same characteristics of Barbara.

Similar traits are capitulum form and type, and plant height in spring flowerings. The ray floret color of both Valerie and Barbara is generally described as dark red-purple. However, the ray floret color of Valerie has more red than the ray floret color of Barbara. In addition, when compared with Barbara, Valerie has a larger diameter of capitulum, a significantly later natural season flower date, a slower response time in controlled flowerings, and a shorter plant height in fall flowerings.

In the following description, color references are made to the Royal Horticultural Society Colour Chart. The color values were determined on plant material grown as a pinched garden mum grown outdoors in Salinas, Calif. on Sep. 3, 1993.

Classification:

*Botanical.*—*Dendranthema grandiflora* cv Valerie.

*Commercial.*—Flat decorative spray pot mum and garden mum.

INFLORESCENCE

A. Capitulum:

*Form.*—Flat.

*Type.*—Decorative.

*Diameter across face.*—35 to 44 mm when fully opened.

B. Corolla of ray florets:

*Color (general tonality from a distance of three meters).*—Dark red-purple.

*Color (upper surface).*—61A to 61B.

*Color (under surface).*—Closest to 78C to 78D.

*Shape.*—Cross section of young ray florets concave, longitudinal section of outer ray florets straight. Petal tips rounded, slightly dentate.

C. Corolla of disc florets:

*Color (mature).*—14B.

*Color (immature).*—14B, overlaid with 144B.

D. Reproductive organs:

*Androecium.*—Present on disc florets only; very few to no disc florets.

*Gynoecium.*—Present on both ray and disc florets.

PLANT

A. General appearance:

*Height.*—28 to 30 cm when grown in fall under natural daylength in New Jersey with no growth regulators, and 15 to 18 cm when grown in 10 cm pots in spring in Salinas with no growth regulator applications.

*Branching pattern.*—Spreading, with 6 to 8 breaks after pinch when grown outside under natural daylength in fall flowerings and with 5 to 6 breaks when grown in 10 cm pots for spring flowerings.

B. Foliage:

*Color (upper surface).*—147A.

*Color (under surface).*—147B.

*Shape.*—See photograph.

Chart A

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

| | VALERIE | BARBARA |
|---|---|---|
| Ray floret color | Dark red-purple | Dark red-purple |
| Capitulum form and type | Flat decorative | Flat decorative |
| Diameter across face of capitulum | 35 to 44 mm | 32 to 41 mm |
| Nat. season flower date: | | |
| in Salinas, CA | Sep 2 to 7 | Aug 18 to 26 |
| in Hightstown, NJ | Oct 7 to 14 | Sep 28 to 30 |
| Controlled response | 54 to 58 days | 49 to 56 days |
| Plant height: | | |
| in natural season fall | 28 to 30 cm | 33 to 41 cm |
| in 10 cm pots spring | 15 to 18 cm | 15 to 18 cm |

I claim:

1. A new and distinct Chrysanthemum plant named Valerie, as described and illustrated.

* * * * *

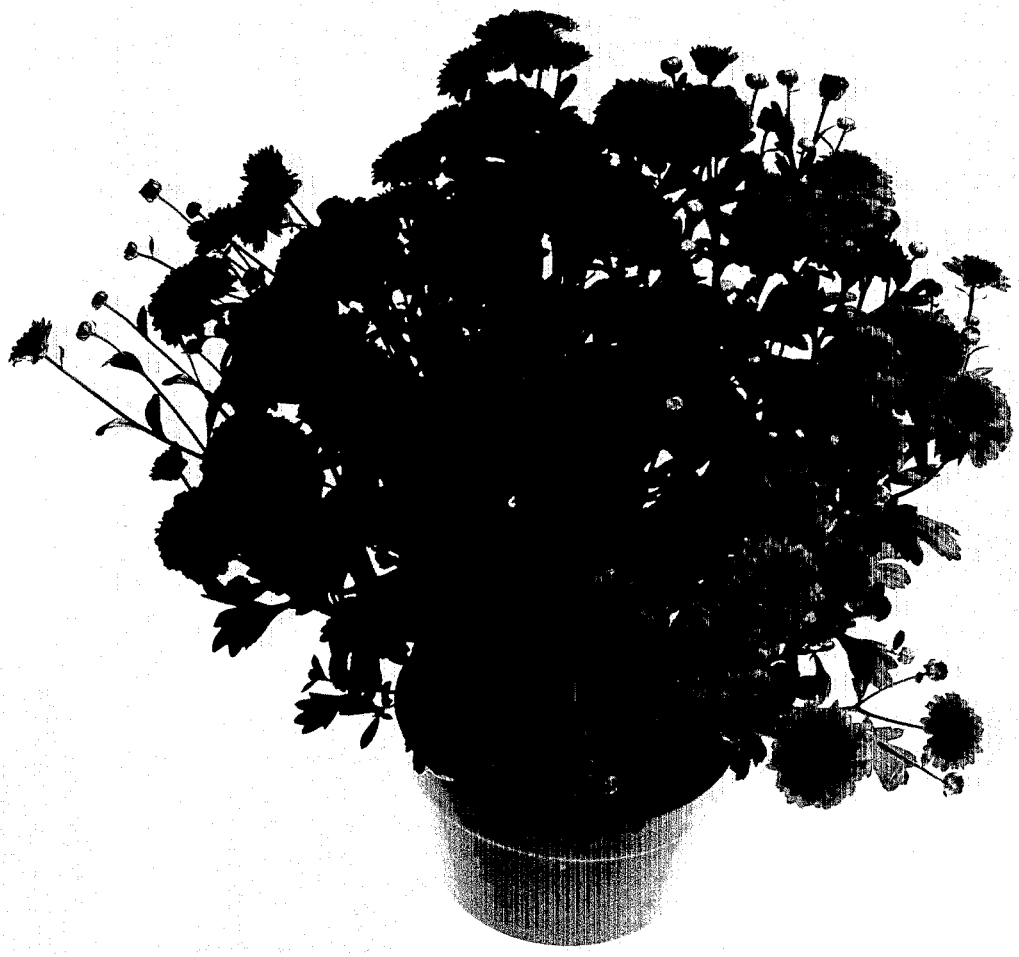

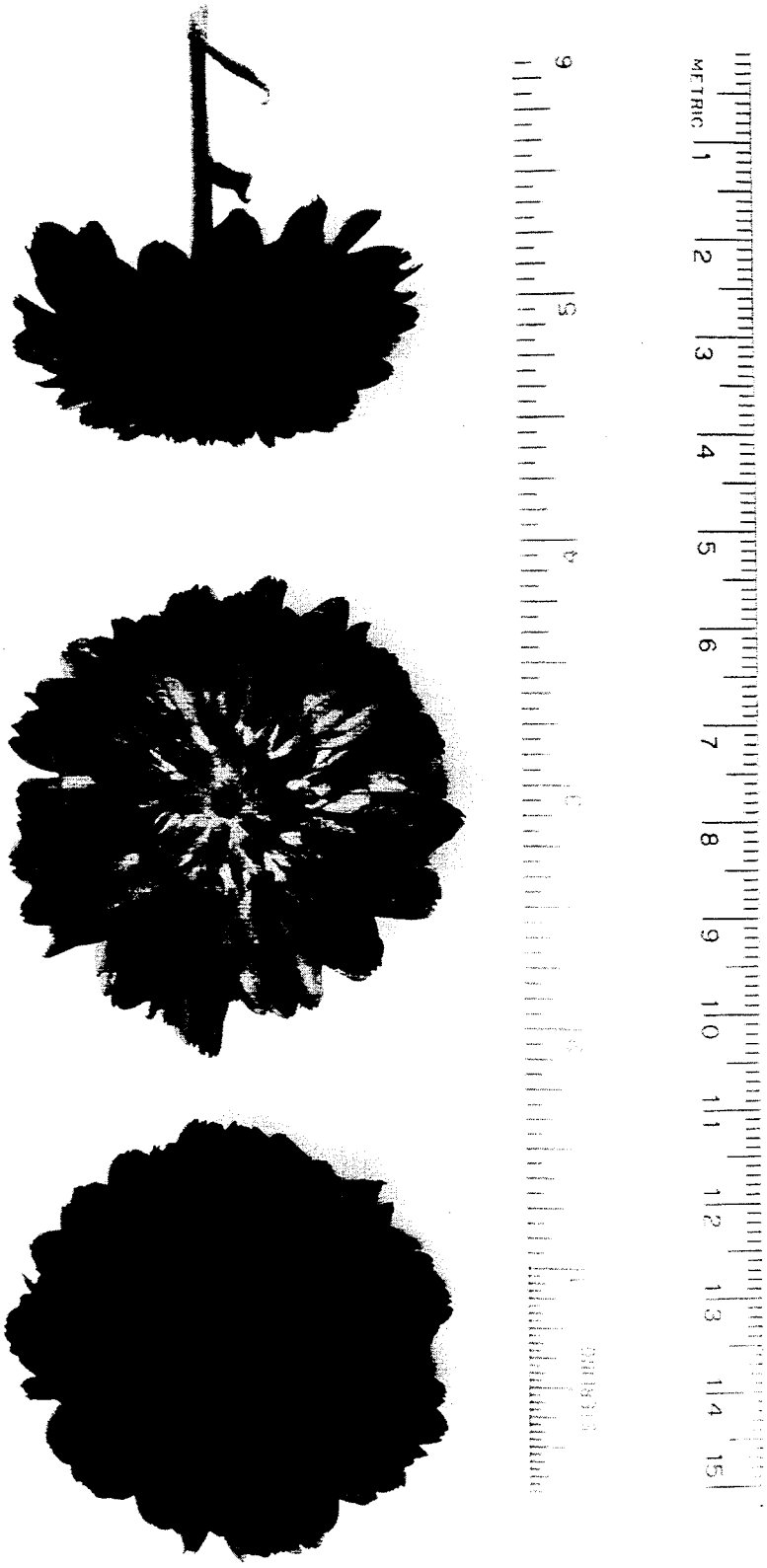
METRIC
1
2
3
4
5
6
7
8
9
10
11
12
13
14
15

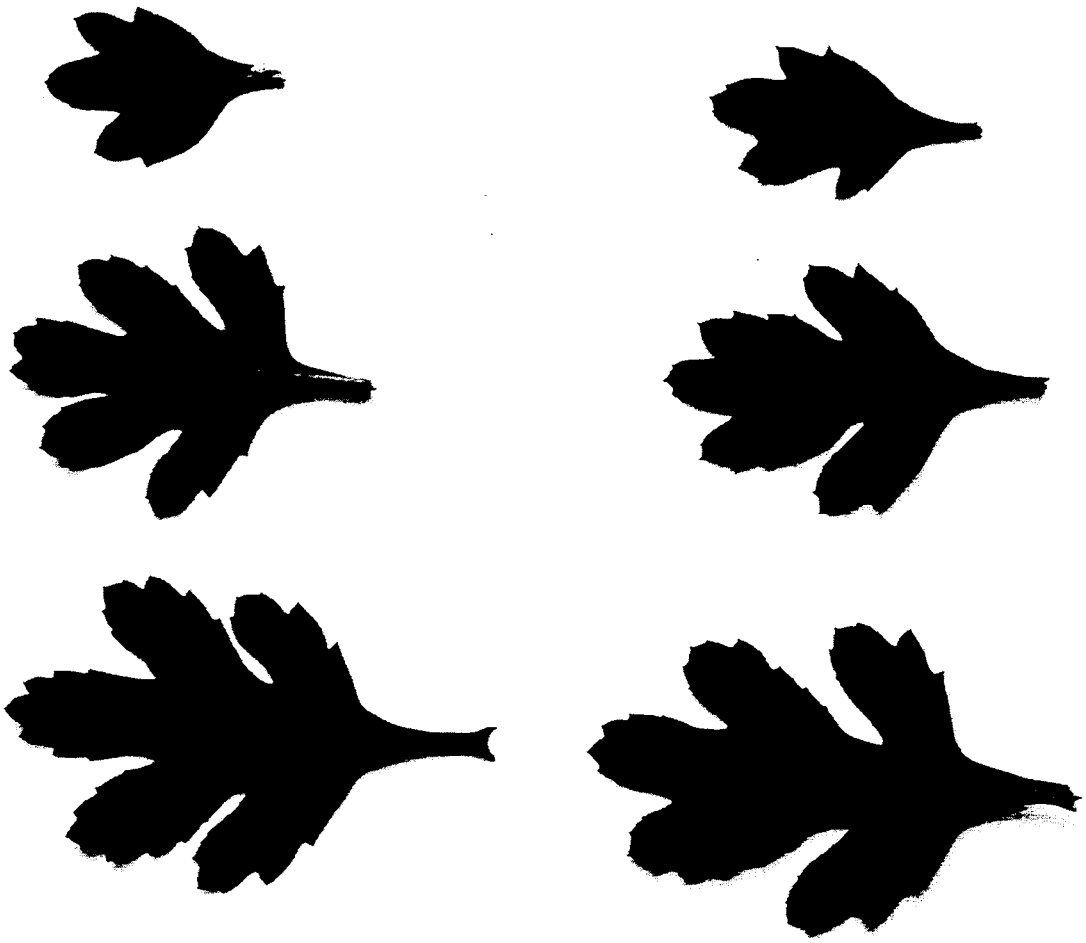
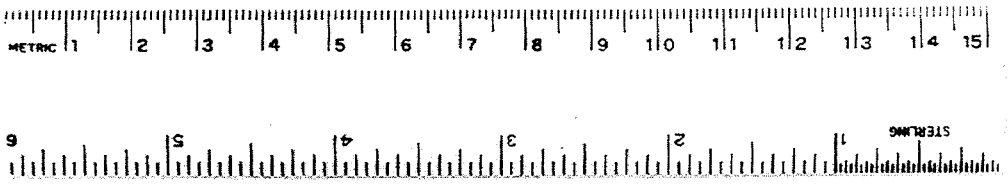
METRIC
1
2
3
4
5
6
7
8
9
10
11
12
13
14
15
STERLING
1
2
3
4
5
6